United States Patent
Landers

(10) Patent No.: US 6,576,673 B2
(45) Date of Patent: Jun. 10, 2003

(54) METHOD OF DETERRING WOODPECKERS

(76) Inventor: Phillip G. Landers, 5312 Vista Club Run, Sanford, FL (US) 32771

( * ) Notice: Subject to any disclaimer, the term of this patent is extended or adjusted under 35 U.S.C. 154(b) by 0 days.

(21) Appl. No.: 10/212,492

(22) Filed: Aug. 5, 2002

(65) Prior Publication Data

US 2003/0026825 A1 Feb. 6, 2003

Related U.S. Application Data

(60) Provisional application No. 60/310,329, filed on Aug. 6, 2001.

(51) Int. Cl.$^7$ ................................................. A61K 31/12
(52) U.S. Cl. ....................................... 514/675; 514/690
(58) Field of Search ................................. 514/675, 690

(56) References Cited

U.S. PATENT DOCUMENTS

| | | |
|---|---|---|
| 4,414,227 A | 11/1983 | Tomlinson, Sr. et al. |
| 4,773,792 A | 9/1988 | Landers |
| 4,905,441 A | 3/1990 | Landers |
| 5,245,812 A | 9/1993 | Landers |
| 6,237,305 B1 | 5/2001 | Landers |

*Primary Examiner*—Alton N. Pryor
(74) *Attorney, Agent, or Firm*—William M. Hobby, III

(57) ABSTRACT

A method of making a coating for deterring woodpeckers from damaging wood using Isophorone and the composition made therefrom. The Isophorone is combined with heated wax and combined with a thickener, such as a clay thickener and a silica thickener, and mixed with an acrylic resin. The composition is cooled and blending with ceramic pellets under a vacuum and dried. The dried pellets are then added to a polymer resin, such as an epoxy resin to form a coating material that will deter woodpeckers.

11 Claims, No Drawings

METHOD OF DETERRING WOODPECKERS

The Appln claims benefit of No. 60/310,329 filed Aug. 6, 2001.

BACKGROUND OF THE INVENTION

The present invention relates to a process for deterring woodpeckers from wood poles, including those sections of the pole repaired as a result of previous woodpecker damage.

Woodpeckers destroy tens of thousands of wood power and telephone poles annually and are the primary cause of above-ground wood pole damage. While hundreds of different chemicals have been tried in an effort to deter woodpeckers from wood poles, none have proven effective in deterring one of the largest of these birds, the Pileated woodpecker. Of the wood pole structures damaged by woodpeckers, the larger and more expensive wood high tension electric transmission line structures are particularly vulnerable to Pileated woodpecker attack.

In the Tomlinson, Sr. et al U.S. Pat. No. 4,414,227, a chemical compound Isophorone (3,5,5-trimethyl-2-cyclohexen-one-1) was painted or applied to a surface of a utility pole and was effective in repelling woodpeckers. The tests were performed on the smaller golden fronted adult woodpeckers. Tomlinson, Sr. et al. also reported that the amount of ketonic compound sufficient to repel woodpeckers is within the range of 0.5 to 3 ounces per square foot of surface. If the compound is encapsulated, the amount of compound can be reduced, for example, to 0.1 ounce per square foot of surface.

A paint was developed, under an exclusive license to the above referenced Tomlinson technology, that incorporates micro-capsules of Isophorone in an acrylic emulsion. This paint, described in my prior U.S. patent application Ser. No. 09/480,352, "Process for In-situ Treatment of Wood Poles", containing 70–80% Isophorone; 8–20% acrylic resin solution; 5–10% paraffin wax; 4–8% clay thickener and 1–2% of a floculated silica thickener, is used to reactivate existing preservatives in the wood.

A four year field evaluation program involving numerous electric utilities throughout the United States was undertaken to evaluate the effectiveness of the Tomlinson, Sr. paint in deterring woodpeckers from transmission line structures. As part of this evaluation, previously woodpecker damaged sections of poles were painted. The total concentration of Isophorone chemical compound was approximately 2 ounces per square foot of surface. Because the micro-capsules of Isophorone were adhered to the wood surface by the acrylic resin, the greatest concentration of the chemical compound resided at or near the surface. After approximately 3–4 years, each pole that had been treated with the paint was evaluated to determine its effectiveness in deterring further woodpecker activity. Results of this field evaluation showed the paint to be effective in reducing further activity by the smaller woodpeckers, however, it did not deter the larger Pileated woodpeckers.

One possible explanation presented for these results is the differing pecking mechanisms employed by different size woodpeckers. Observations indicate that the smaller, less-powerful woodpeckers require a higher number of pecks to penetrate the wood, while the larger, more powerful Pileated woodpeckers are able to rip the wood with a minimal number of pecks, removing sections as large as ½" thick and 4–6" in length. In summary, it appears that the high repetition—low power pecking technique employed by smaller woodpeckers ruptures a sufficient number of micro-capsules on the wood's surface to be deterred. In contrast, by being able to remove relatively large portions of the pole's surface with a minimal number of powerful pecks, an insufficient number of micro-capsules are ruptured to deter the Pileated woodpecker from the pole.

SUMMARY OF THE INVENTION

A method of making a coating for deterring woodpeckers from damaging wood using Isophorone and the composition made therefrom. The Isophorone is combined with heated wax and combined with a thickener, such as a clay thickener and a silica thickener, and mixed with an acrylic resin. The composition is cooled and blending with ceramic pellets under a vacuum and dried. The dried pellets are then added to a polymer resin, such as an epoxy resin to form a coating material that will deter woodpeckers.

DESCRIPTION OF THE PREFERRED EMBODIMENT

The present invention describes a method of deterring woodpeckers, including Pileated woodpeckers, from wood structures. Capsules containing the chemical compound Isophorone are blended into a high-strength, closed-cell structural foam, either syntactic or expanding, epoxy or other polymer, and the structural matrix applied into or onto the pole. The high strength matrix can be used to strengthen and repair wood poles damaged by woodpeckers, as seen in my prior U.S. Pat. Nos. 4,905,441 and 5,245,812, or applied to the surface of wood poles to deter woodpeckers from the pole.

The present invention includes the encapsulation of the proven woodpecker deterring Isophorone chemical compound capsules in a high strength matrix versus simply applying the capsules to the pole's surface with an adhesive or coating material. The high strength matrix prevents the easy removal of the capsules by the woodpecker thus requiring more "pecks"; resulting in a larger number of capsules ruptured; and a higher volume of deterring Isophorone chemical compound being released.

Isophorone encapsulation in this high-strength matrix is applicable to both surface and in-hole repair applications.

The use of a high-strength matrix is accomplished by mixing the Isophorone within a structural polymer matrix, either unfoaming or foaming, syntactic or expanding, epoxy or other polymer which can be used to repair woodpecker holes which in turn prevents woodpeckers, such as Pileated woodpeckers, from damaging an already repaired pole. A matrix of the Isophorone chemical compound in the structural polymer forms a high-strength matrix which can be applied to the surface to not only prevent the smaller woodpeckers from attacking the pole but also protects the poles from the Pileated woodpecker.

EXAMPLE

A specific Isophorone compound formula includes 77.5% Isophorone, 10% solution acrylic resin, 5.6% of paraffin wax, 5.3% of a clay thickener, and 1.6% of a flocculated silica thickener. The Isophorone is obtained from Union Carbide while the acrylic resin is obtained from Rohm and Haas under their formula Acryloid B-66. Paraffin wax is obtained from the International Group, Inc., Item #1260. The clay thickener is Claytone APA from Southern Clay Products and the flocculated silica thickener is Degusa Aerosil 200. The paraffin wax is heated to melt it and then combined with the Isophorone and, while heated, the clay thickener and the flocculated silica thickener are added to the mixture which is blended together. The composition is allowed to cool to ambient temperature and the solution acrylic resin is added to the cooled mixture. This Isophorone compound is then blended under total vacuum with an equal amount of porous ceramic pellets, after which the pellets are allowed to dry. The porous ceramic pellets are Verilite obtained from Harbinson-Walker Refractories Company. The dried pellets are added to IFOAM expanding epoxy polymer concrete which is described in U.S. Pat. No. 4,773,792, System for Stabilizing Structural Elements, by the present inventor. The IFOAM is obtained from ICORP-IFOAM Speciality Products Corporation, 250 Power Court, Sanford, Fla. 32771.

Dried pellets from encapsulating the Isophorone compound are added to the epoxy resin and the epoxy catalyst is mixed with the resin just prior to being used. Once the resin with the encapsulating pellets is mixed with the catalyst, the compound is painted onto a surface, such as a wooden utility pole, covering the surface of the pole for protection from woodpeckers. The epoxy compound forms a rigid foamed compound which cures rapidly, such as in 30 minutes, which becomes thick coating of a foamed polymer. Woodpeckers attacking the coated wood poles break the ceramic microcapsules to release the Isophorone compound to deter further woodpecker activity.

It should be clear at this time that a new method of deterring woodpeckers, especially larger woodpeckers such as the Pileated woodpeckers, from attacking utility poles and the like has been provided. It should, however, also be clear that the present invention is not intended to be limited to the forms shown which are to be considered illustrative rather than restrictive.

I claim:

1. A method of making a coating for deterring woodpeckers from damaging wood comprising the steps of combining heated wax and Isophorone mixing in a thickener into the wax and the Isophorone mixture;

mixing in an acrylic resin to the heated wax; the Isophorone and the thickener to form a composition;

cooling the composition;

blending in ceramic pellets with the composition under a vacuum;

drying said composition mixed with said ceramic pellets to form ceramic capsules; and mixing said ceramic capsules with a polymer resin to form a coating having said ceramic capsules therein; thereby forming a coating for wood which deters woodpeckers.

2. The method of making a coating for deterring woodpeckers from damaging wood in accordance with claim 1 in which said step of mixing said thickener includes mixing a clay thickener.

3. The method of making a coating for deterring woodpeckers from damaging wood in accordance with claim 2 in which said step of mixing the thickener includes mixing a flocculated silica thickener.

4. The method of making a coating for deterring woodpeckers from damaging wood in accordance with claim 1 in which said step of mixing ceramic capsules includes mixing an epoxy resin and an epoxy hardener.

5. A method of making a woodpecker deterrent comprising the steps of:

mixing Isophorone with heated wax and a thickener to form a mixture;

cooling said mixture;

blending ceramic pellets with said cooled mixture to form a composition; and drying said composition to form a woodpecker deterrent for blending into a wood coating material.

6. The method of making the woodpecker deterrent in accordance with claim 5 including the step of mixing said woodpecker deterrent with an epoxy resin and an epoxy hardener for coating onto a wood surface.

7. The method of making the woodpecker deterrent in accordance with claim 6 in which the step of mixing said Isophorone with said heated wax and said thickener includes mixing with a flocculated silica thickener.

8. The method of making the woodpecker deterrent in accordance with claim 7 in which the step of mixing said Isophorone with said heated wax and said thickener includes mixing with a clay thickener.

9. The method of making the woodpecker deterrent in accordance with claim 5 including the step of mixing in an acrylic resin to the Isophorone and the heated wax and the thickener mixture.

10. The method of making the woodpecker deterrent in accordance with claim 9 in which the step of drying includes vacuum drying said mixture of said Isophorone, said heated wax and said thickener with said ceramic pellets.

11. A woodpecker deterrent composition comprising:

Isophorone; heated wax; clay thickener; acrylic resin; ceramic pellets; and a polymer resin blended to form a wood coating material which deters woodpecker damage to wood.

\* \* \* \* \*